(12) United States Patent
Aviv et al.

(10) Patent No.: US 6,884,220 B2
(45) Date of Patent: Apr. 26, 2005

(54) OPTICAL TRANSESOPHAGEAL ECHOCARDIOGRAPHY PROBE

(75) Inventors: Jonathan E. Aviv, New York, NY (US); Shunichi Homma, New York, NY (US); Marco R. DiTullio, New York, NY (US); Steven Corwin, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 203 days.

(21) Appl. No.: 10/188,357

(22) Filed: Jul. 1, 2002

(65) Prior Publication Data

US 2003/0036681 A1 Feb. 20, 2003

Related U.S. Application Data

(60) Provisional application No. 60/302,410, filed on Jun. 29, 2001.

(51) Int. Cl.[7] .................................................. A61B 8/14
(52) U.S. Cl. ....................................................... 600/462
(58) Field of Search ................................. 600/129, 130, 600/160, 300, 407–472, 476, 478; 128/898, 897, 916

(56) References Cited

U.S. PATENT DOCUMENTS

| | | | |
|---|---|---|---|
| 4,319,563 A | 3/1982 | Kubota | |
| 4,327,738 A | 5/1982 | Green et al. | |
| 4,375,818 A | 3/1983 | Suwaki et al. | |
| 4,567,882 A | 2/1986 | Heller | |
| 4,605,009 A | 8/1986 | Pourcelot et al. | |
| 4,977,898 A | 12/1990 | Schwarzschild et al. | |
| 5,050,584 A | 9/1991 | Matsuura | |
| 5,083,549 A | 1/1992 | Cho et al. | |
| 5,105,819 A | 4/1992 | Wollschlager et al. | |
| 5,181,514 A | * 1/1993 | Solomon et al. | 600/444 |
| 5,213,093 A | 5/1993 | Swindle | |
| 5,217,456 A | 6/1993 | Narciso, Jr. | |
| 5,299,578 A | * 4/1994 | Rotteveel et al. | 600/463 |
| 5,382,231 A | 1/1995 | Shlain | |
| 5,469,852 A | * 11/1995 | Nakamura et al. | 600/463 |
| 5,512,035 A | * 4/1996 | Konstorum et al. | 600/146 |
| 5,671,748 A | 9/1997 | Itoi | |
| 5,749,883 A | 5/1998 | Halpern | |
| 5,799,655 A | 9/1998 | Jang et al. | |
| 6,358,197 B1 | * 3/2002 | Silverman et al. | 600/29 |

* cited by examiner

*Primary Examiner*—Ali Imam
(74) *Attorney, Agent, or Firm*—William H. Dippert; Reed Smith LLP

(57) ABSTRACT

The present invention concerns an optical transesophageal echocardiography probe (OPTEE) having an optical fiber bundle, a suction channel and light channels for illumination, wherein the OPTEE has a circumference along its distal tip that allows both safe insertion and insures the stability of the probe. The probe tip is generally circular in circumference, but levels off to a flat surface for a portion of the circumference, and is provided with beveled edges and corner throughout so that there are no sharp edges to traumatize the patient. The invention also concerns an optically-recessed OPTEE comprising an optical transesophageal probe comprising a longitudinally extending main body having an outer surface and a substantially circular cross-section and a distal portion having an outer surface and a distal tip, wherein an optical bundle having a distal tip is positioned on the outer surface of the main body and the outer surface of the distal portion and the distal tip of the optical bundle does not extend as far as the distal tip of the distal portion.

19 Claims, 3 Drawing Sheets

OPTICAL TRANSESOPHAGEAL ECHOCARDIOGRAPHY PROBE

CROSS-REFERENCE TO RELATED APPLICATION

This application is based upon commonly assigned U.S. provisional patent application Ser. No. 60/302,410, filed Jun. 29, 2001, now abandoned.

FIELD OF THE INVENTION

The present invention relates to an optical transesophageal echocardiography probe (OPTEE). More particularly, the present invention relates to an optical transesophageal echocardiography probe having an optical fiber bundle to allow real-time visualization of the structures that are transversed as the OPTEE is passed via the mouth into the esophagus, wherein the probe has a unique profile which allows passage into the esophagus with a minimum amount of trauma to the patient.

BACKGROUND OF THE INVENTION

Clinical experience with traditional transesophageal echocardiography (TEE) has shown that a number of patients have experienced significant complications as a result of the standard blind passage of the probe via the mouth into the esophagus. By "blind", it is meant that the traditional TEE probe never had a way for the physician passing the probe to actually see where he or she was going as the probe was passed via the mouth into the throat and then into the esophagus. The delicate voice box and throat structures sit directly between the mouth and the esophagus. All other medical and surgical specialties passing instruments in this area do so under direct, real-time visualization. Since approximately 30% of patients undergoing TEE are completely anti-coagulated, the risk of significant injury to the vocal cords and throat when a patient's blood is thin is great. As the standard TEE probe is quite large in diameter—approximately 15 mm (as opposed to most GI and ENT endoscopes, which are around 3–8 mm)—passing such a large instrument without seeing precisely where it is going can, and often does, results in considerable untoward complications for the patient. These complications have included perforation of the hypopharynx and esophagus, tearing of the throat tissues, and vocal cord injury. The solution to this problem is to develop a TEE probe that provides the probe passer, i.e., the physician, with the ability to actually see what structures he or she is traversing on the way from the mouth to the esophagus.

A number of prior art references are known:

U.S. Pat. No. 5,749,833, which issued to Hakki et al. on May 12, 1998, discloses an esophageal probe with a rounded tip for ease of insertion;

U.S. Pat. No. 4,567,882, which issued to Heller on Feb. 4, 1986, discloses an endotracheal tube with a fiberoptic light conducting means;

U.S. Pat. No. 5,382,231, which issued to Shlain on Jan. 17, 1995, discloses a transesophageal probe with light conducting and suction means;

U.S. Pat. No. 5,105,819, which issued to Wollschlager et al. on Apr. 21, 1992, discloses a probe for use in transesophageal echocardiography;

U.S. Pat. No. 4,327,738, which issued to Green et al. on May 4, 1982, discloses an endoscope for use in esophageal probes utilizing optical means to aid the user by direct viewing of the area being intubated;

U.S. Pat. No. 4,605,009, which issued to Pourcelot et al. on Aug. 12, 1986, discloses an optical viewing endoscope having utility in the esophagus. An ultrasonic imaging means for internal organs is employed with the optical means;

U.S. Pat. No. 5,505,584, which issued to Matsuura on Sep. 24, 1991, discloses an endoscope with a reduced size distal tip to mitigate pain during insertion;

U.S. Pat. No. 5,217,456, which issued to Narciso on Jun. 8, 1993, discloses an intra-vascular optical imaging system;

U.S. Pat. No. 5,213,093, which issued to Swindle on May 25, 1993 discloses an intravascular optical imaging system; and U.S. Pat. No. 4,319,563, Kubota on Mar. 16, 1982, discloses an endoscopic device having a distal end face formed into a smooth, spherical convexity.

OBJECTS OF THE INVENTION

It is therefore an object of the present invention to provide a transesophageal echocardiography probe which allows real-time visualization of the structures that are traversed as the probe is passed via the mouth into the esophagus.

It is also an object of the invention to provide a transesophageal echocardiography probe which allows for the direct suctioning of secretions and debris that may obscure direct passage of the probe into the esophagus.

It is a further object of the present invention to provide a transesophageal echocardiography probe which reduces the trauma experienced by the patient upon insertion and passage of the TEE probe through the mouth to the esophagus.

It is yet another object of the present invention to provide a transesophageal echocardiography probe which possesses a cross-sectional configuration such that the TEE probe more easily and smoothly passes into a patient's esophagus.

It is a yet further object of the present invention to provide a transesophageal echocardiography probe which has an optically-recessed fiber bundle.

These and other objects of the invention will become more apparent from the discussion below.

SUMMARY OF THE INVENTION

The present invention provides for an optical transesophageal echocardiography probe having an optical fiber bundle to allow real-time visualizations of the structures that are transversed as the OPTEE is passed via the mouth into the esophagus. The probe has a unique profile which allows passage into the esophagus with a minimum amount of trauma to the patient.

In one embodiment the transesophageal echocardiography probe of the present invention is provided with a specially designed circumference along its distal tip that allows both safe insertion for the patient and insures stability of the ultrasound portion of the probe tip. Patient safety is enhanced by making most of the probe tip circumference a circular shape. The stability of the ultrasound transducer is enhanced by having the round shape level off to a flat surface. The transition from a round profile to a flat profile is made by beveling the edges of the endoscope along its distal tip. Beveling the edges of the probe tip also decreases the chance of a probe edge lacerating tissue surfaces in the patient's passageway.

In another embodiment of the invention the TEE probe has an optically-recessed fiber bundle. This configuration facilitates visualization of the actual tip of the TEE probe while allowing real-time visualization of the structures that are traversed as the TEE probe is passed via the mouth into the esophagus. Preferably this embodiment has a small suction channel for directly suctioning secretions and debris that may obscure direct passage of the probe into the esophagus.

The construction and obvious advantages of the system provided for by the present invention will become more clearly understood from the following description of the various specific embodiments when read in conjunction with the accompanying drawings.

DETAILED DESCRIPTION OF THE INVENTION

The present invention is directed to an optical transesophageal echocardiography probe having an optical fiber bundle to allow real-time visualizations of the structures that are transversed as the OPTEE is passed via the mouth into the esophagus. The probe has a unique profile which allows passage thereof into the esophagus with a minimum amount of trauma to the patient.

In one embodiment the probe of the invention has at least the following distinguishing features:

1. The present invention provides for the first echocardiography probe to have channels for optics and for suction.
2. The OPTEE probe tip has a flat inferior surface that tapers from a circular profile, thus slightly narrowing its diameter and shape towards its tip. This allows for smoother insertion into the esophagus while still permitting flat contact between the ultrasound sensor and the esophageal wall.
3. The point where the probe shifts from circular to a circle-with-flat-inferior-aspect contains beveled edges so as to minimize trauma.

The present invention solves the problem of blindly passing a large caliber probe over some of the most delicate structures that exist in the head and neck. In addition, direct visualization of TEE probe passing will necessarily reduce some of the most severe, lifethreatening complications of this procedure such as perforation of the throat and esophagus, tearing of the throat tissues, vocal cord damage and traumatic airway obstruction.

The transesophageal echocardiography probe of the present invention in a first embodiment is provided with a specially designed configuration along its distal tip that allows both safe insertion for the patient and insures stability of the ultrasound portion of the probe tip. The stability of the ultrasound transducer is enhanced by having the round shape level off to a flat surface. The transition from a round profile to a flat profile is made by beveling the edges of the endoscope along its distal tip and lateral edges. Beveling the edges of the probe tip also diminishes the chance of a probe edge lacerating tissue surfaces in the patient's passageway.

In another embodiment of the invention the probe has an optically recessed tip. More particularly, the distal tip of a longitudinally extending optical fiber bundle ends a set distance short of the actual distal end of the distal tip. In addition, there is a suction channel to remove debris and help keep the viewing field clear.

Figure 3:
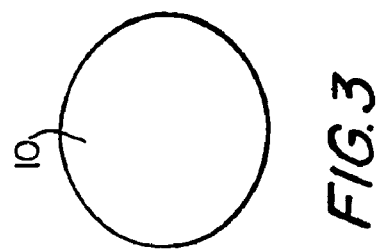
FIG. 3 is a schematic representation of a cross-sectional view across line 3—3 of the main section of the embodiment of an optical transesophageal echocardiography probe shown in FIG. 1.
Figure 2:
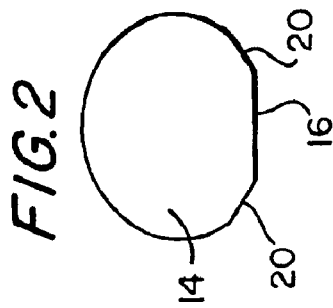
FIG. 2 is a schematic representation of a cross-sectional view across line 2—2 of the end sectional view of the optical transesophageal echocardiography probe shown in FIG. 1.
Figure 1:
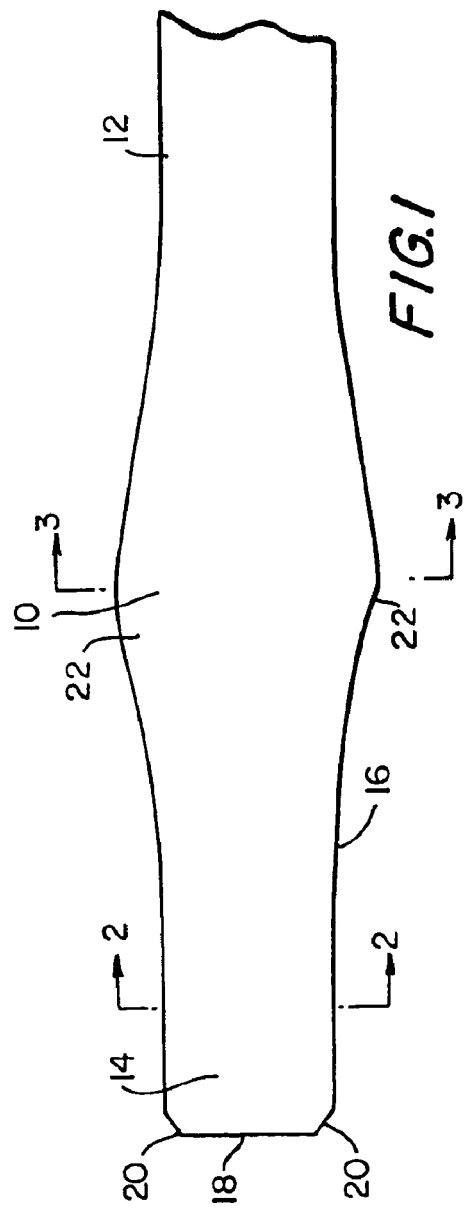
FIG. 1 is a schematic representation of a side elevational view of the distal end of one embodiment of an optical transesophageal echocardiography probe according to the invention.
Figure 1A:
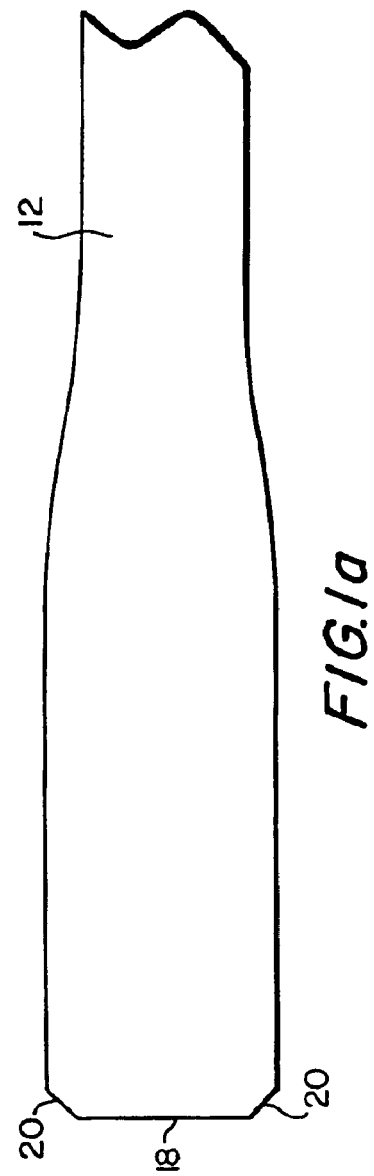
FIG. 1A is a top view of the embodiment of an optical transesophageal echocardiography probe shown in FIG. 1.

The invention can perhaps be better appreciated from the drawings. FIGS. 1 to 3 are schematic representations of side elevational, top, and cross-sectional views of the distal portion of an optical transesophageal echocardiography probe according to the invention. A distal portion 10 of a probe shaft 12 is a transition zone between substantially circular cross-section 12 and flat-bottomed, bevel edged tip 14, which has a lower flat surface 16. A distal end 18 of tip 14 has beveled edges 20, as are transition portions 22 from portion 10 to tip 14 and, optionally, edges of flat surface 16.

A probe according to the invention will typically be about 100 cm long and be flexible and steerable, preferably in the up and down directions. Also, typically the diameter of the probe shaft will be about 10–12 mm and the diameter of the probe distal portion will be about 1–2 mm greater in the first embodiment and about 6–8 mm greater in the second embodiment described below. The probes will also have construction elements, e.g., proximal control units, similar to TEE probes sold by Agilent/Philips and Siemens, as would be appreciated by those skilled in the art. With regard to the embodiment set forth in FIGS. 1 to 3, the effective vertical dimension of the cross-section of tip 14 will be preferably about the same as the diameter of probe shaft 12, and the effective horizontal dimension of the cross-section of tip 14 will be from about 1.2 to about 2.0, preferably from about 1.3 to about 1.7, times the diameter of probe shaft 12 or distal portion 10. The diameter of distal portion 10 will be substantially equal to, or preferably slightly greater than, the diameter of probe shaft 12. It is within the scope of the invention that the horizontal dimension of the cross-section of tip 14 and/or the cross-section of distal tip 18 can be less than described before, even less than the diameter of shaft 12, so long as the vertical dimension of the cross-sectional area is no greater than substantially equal to or less than the effective diameter of distal portion 10 or the diameter of probe shaft 12.

Figure 4:
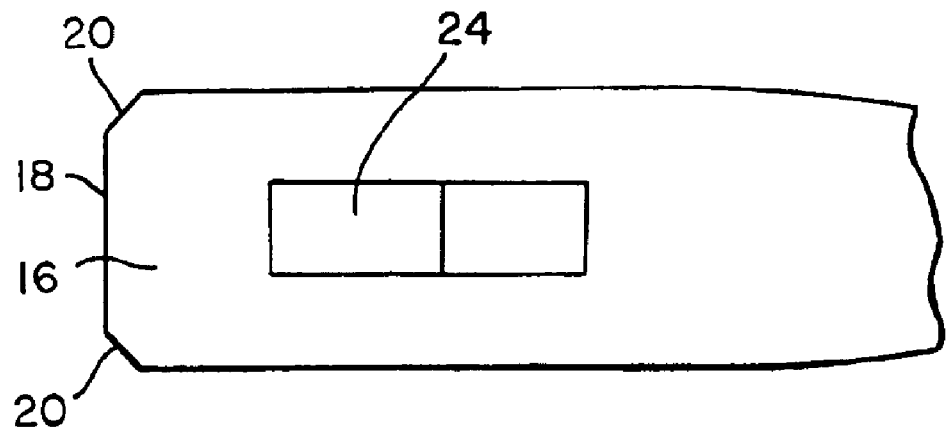
FIG. 4 is a schematic representation of a bottom view showing the undersurface of the distal end of the embodiment of an optical transesophageal echocardiography probe shown in FIG. 1.

FIG. 4 is a schematic representation of a bottom view of the distal portion 10 of the optical transesophageal echocardiography probe 12 of FIGS. 1 to 3. Flat surface 16 of tip 14 has viewing window or windows 24. Optionally surface 16 can comprise one or more ultrasound transducers as element 24. Also shown are beveled edges 20.

Figure 5:
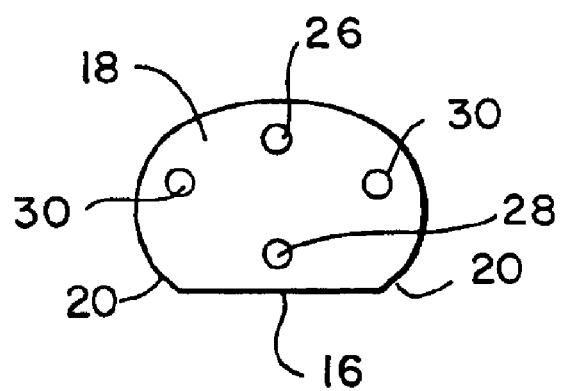
FIG. 5 is a schematic representation of an end longitudinal view of the embodiment of an optical transesophageal echocardiography probe shown in FIG. 1 showing the various fiberoptic, suction and light channels located therein.

FIG. 5 is a schematic representation of an end cordinal view of the transesophageal echocardiography probe according to FIGS. 1 to 3. Shown are flat surface 16 of tip 14. Also shown are optional fiberoptic cable channel 26, suction channel 28, and illumination channels 30.

Figure 6:
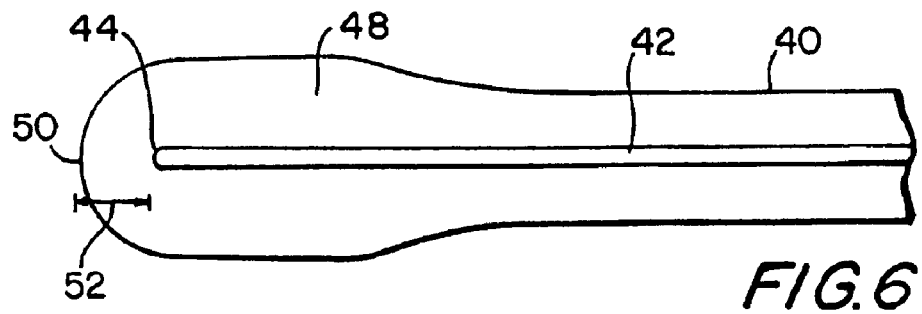
FIG. 6 is a schematic representation of the distal end of the dorsal surface of another embodiment of an optical transesophageal echocardiography probe according to the invention.

In the embodiment of the invention shown in FIG. 6 in a dorsal view, a TEE probe 40 has a longitudinally extending optical bundle 42 arranged opposite to an ultrasound transducer site (not shown). Optical bundle 42, which preferably comprises a fiber optic bundle of illumination and viewing fibers, terminates in distal end 44 on probe distal portion 48. Channel distal end 44 is not coexistensive with distal end 50 of TEE probe 40 and terminates short of distal end 50 a sufficient distance 52 to facilitate visualization of distal end 50. The site of distal end 44 can be adjusted or varied. However, distal end 44 is intended to provide a viewing field that preferably partly includes a portion of distal end 50 so that the physician can visualize distal end 50 with regard to the structures being traversed. Preferably the distance 52 between distal end 44 and distal end 50 is from about 5 mm to about 10 mm, more preferably from about 1 to 8 mm.

Figure 7:
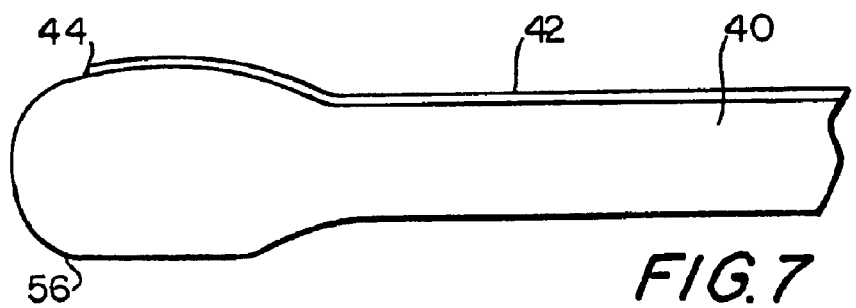
FIG. 7 is a schematic representation of a lateral view of the distal end of the probe shown in FIG. 6.

As shown in FIG. 7, optical bundle 42 of TEE probe 40 is slightly recessed in the outer surface of probe 40. Preferably bundle 42 is sufficiently recessed that the working profile of probe 40 is substantially the same as it would be without bundle 42.

Figure 8:
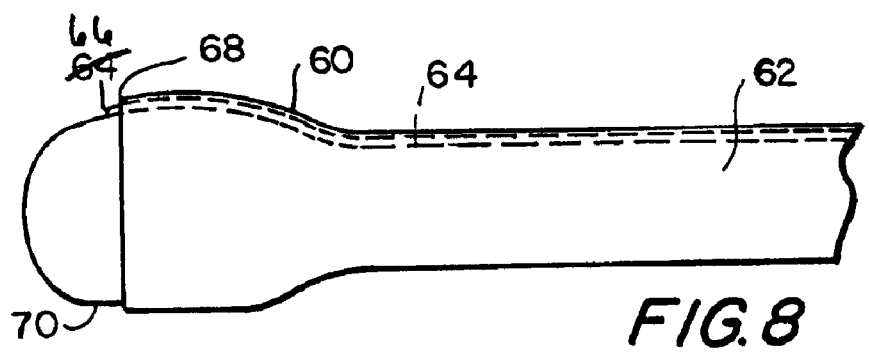
FIG. 8 is a schematic representation of a lateral view of the embodiment of FIGS. 6 and 7 with a sheath.

As shown in FIGS. 6 and 7, optical bundle 42 can be positioned opposite the flat transducer surface 58, and optical bundle 52 can be slightly recessed in a groove or channel in the outer surface of probe 40. It is also within the scope of the invention that there could be more than on optical bundle 42 and that each bundle 42 could be positioned other than directly opposite transducer surface 56. Also, each optical bundle 42 need not be recessed but could be affixed or adhered to the outer surface of probe 40 with glue, bands, or the like. In one embodiment, as shown in FIG. 8, a sheath 60 arranged around a probe 62 holds an optical bundle 64 (shown in dotted lines) in position between sheath 60 and probe 62, where the distal end 66 of bundle 64 is at or slightly distal to the distal end 68 of sheath 60. Sheath 60 may have a cutout section (not shown) so that it does not cover any transducer in transducer surface 70. Alternatively, a combination of a less extending sheath and other means to keep the optical bundle in place, may be used.

It will be further apparent to one skilled in this art that the improvements provided for in the present invention, while described with relation to certain specific physical embodiments also lend themselves to being applied in other physical arrangements not specifically provided for herein, which are nonetheless within the spirit and scope of the invention taught here.

We claim:

1. An optical transesophageal echocardiography probe comprising
   a flexible tubular probe shafts having a distal end;
   a transition zone at the shaft distal end having a generally circular cross-section;
   and
   a probe tip attached to the shaft distal end and having a substantially circular cross-section,
   wherein said probe tip has a an exterior flat surface extending longitudinally and wherein the probe configuration facilitates visualization distal to the probe tip during insertion into a patient's esophagus.

2. The probe of claim 1, wherein said probe tip has a rounded distal end.

3. The probe of claim 1, wherein edges of the probe tip are beveled.

4. The probe of claim 1, wherein the transition zone has edges that are beveled.

5. The probe of claim 1, wherein the probe also comprises at least one viewing channel, at least one suction channel, and at least one illumination channel.

6. The probe of claim 1, wherein the horizontal dimension of the cross-section of probe tip is substantially equal to or greater than the diameter of the probe shaft.

7. The probe of claim 6, where the horizontal dimension of the cross-section of probe tip is from about 1.2 to about 2.0 times the diameter of the probe shaft.

8. The probe of claim 1, wherein the vertical dimension of the cross-section of probe tip is equal to or slightly less than the diameter of the probe shaft.

9. The probe of claim 8, wherein the vertical dimension of the cross-section of distal tip is slightly less than the diameter of the probe shaft.

10. An optical transesophageal probe comprising a longitudinally extending, flexible tubular main body having an outer surface and a substantially circular cross-section and a distal portion having an outer surface and a distal tip, wherein an optical bundle having a distal tip is positioned on the outer surface of the main body, wherein the outer surface of the distal portion and the distal tip of the optical bundle do not extend as far as the distal tip of the distal portion and wherein the probe configuration facilitates visualization distal to the probe tip during insertion into a patient's esophagus.

11. The probe of claim 10, wherein the probe distal portion has a flat surface.

12. The probe of claim 11, where the flat surface is a lateral flat surface that comprises one or more ultrasound transducers.

13. The probe of claim 10, wherein the optical bundle comprises an illumination source and a viewing means.

14. The probe of claim 13, where the optical bundle comprises fiber optic fibers that deliver illumination and transmit an image to a viewer or viewing means.

15. The probe of claim 10, wherein there is more than one optical bundle.

16. The probe of claim 10 wherein one optical bundle is positioned opposite to a lateral flat surface.

17. The probe of claim 10, wherein all or a portion of the optical bundle is partly received in a groove or channel in the outer surface of the main body and/or the distal portion.

18. The probe of claim 10, wherein all or a portion of each optical bundle is affixed or adhered to the outer surface of the main body and/or distal portion.

19. The probe of claim 18, wherein a sheath encircles at least a portion of the outer surface of the main body and/or the distal portion.

* * * * *